United States Patent [19]

Frishberg et al.

[11] 4,391,886
[45] Jul. 5, 1983

[54] METHINE COLORANT MATERIALS AND THE USE THEREOF IN ELECTROPHORETIC MIGRATION IMAGING LAYERS AND PROCESSES

[75] Inventors: Mark D. Frishberg; James J. Krutak, Sr., both of Kingsport, Tenn.

[73] Assignee: Eastman Kodak Company, Rochester, N.Y.

[21] Appl. No.: 289,574

[22] Filed: Aug. 3, 1981

Related U.S. Application Data

[62] Division of Ser. No. 161,705, Jun. 23, 1980, Pat. No. 4,304,908.

[51] Int. Cl.³ .................... G03G 13/00; G03G 5/06
[52] U.S. Cl. ........................... 430/41; 430/77; 430/78
[58] Field of Search ................... 430/41, 77, 78

[56] References Cited

U.S. PATENT DOCUMENTS 4,256,819  3/1981  Webster et al. ............... 430/41

Primary Examiner—John D. Welsh
Attorney, Agent, or Firm—J. Frederick Thomsen; Daniel B. Reece, III

[57] ABSTRACT

Disclosed are novel methine colorant materials having the structure

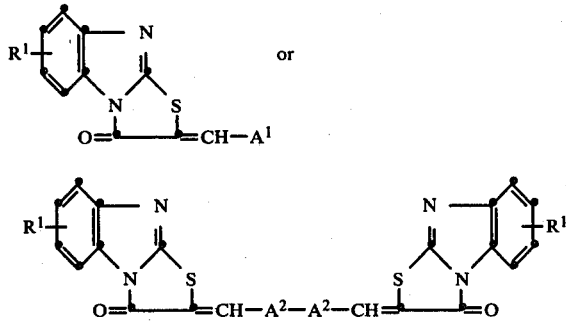

Also disclosed is the use of such materials in electrophoretic migration imaging layers and processes.

19 Claims, 1 Drawing Figure

FIG. 1

METHINE COLORANT MATERIALS AND THE USE THEREOF IN ELECTROPHORETIC MIGRATION IMAGING LAYERS AND PROCESSES

This is a division of application Ser. No. 161,705 filed June 23, 1980, now U.S. Pat. No. 4,304,908, Dec. 8, 1981.

FIELD OF THE INVENTION

This invention relates to electrophoretic migration imaging layers and processes and, in particular, to a novel group of yellow methine colorants and to their use in electrically photosensitive materials in such layers and processes. Such processes are sometimes referred to as photoelectrophoresis, manifold imaging and photosolography.

BACKGROUND OF THE INVENTION

In the past, there has been extensive description in the patent and other technical literature of electrophoretic migration imaging processes. A description of electrophoretic migration imaging processes may be found in U.S. Pat. Nos. 2,758,939 by Sugarman issued Aug. 14, 1956; 2,940,847; 3,100,426; 3,140,175 and 3,143,508, all by Kaprelian; 3,384,565, 3,384,488 and 3,615,558, all by Tulagin et al; 3,384,566 by Clark; 3,383,993 by Yeh; and U.S. Pat. No. 3,976,485 by Groner.

In each of the foregoing electrophoretic migration imaging processes an imaging layer comprising electrically photosensitive particulate material is subjected to the influence of an electric field and exposed to an image pattern electromagnetic radiation to which the electrically photosensitive material is sensitive. The electrically photosensitive material is caused to imagewise migrate electrophoretically in the layer to form a record of the imaging electromagnetic radiation.

In any case, regardless of the particular electrophoretic migration imaging process employed, it is apparent that an essential component of any such process is the electrically photosensitive material. And, of course, to obtain an easy-to-read visible image it is important that the electrically photosensitive material be colored, as well as electrically photosensitive. Accordingly, there exists a continuing effort to find materials which possess both useful levels of electrical photosensitivity and which exhibit good colorant properties. Thus, various types of electrically photosensitive materials are disclosed for use in electrophoretic migration imaging processes.

Up to now, useful electrically photosensitive colorant materials for electrophoretic migration imaging have been selected from known classes of photoconductive materials which may be employed in conventional photoconductive elements, e.g., photoconductive plates, drums, or webs used in electrophotographic office copier devices. For example, both Sugarman and Kaprelian in the above-referenced patents state that electrically photosensitive materials useful in electrophoretic migration imaging processes may be selected from known classes of photoconductive materials. Also, the phthalocyanine pigments described as a useful electrically photosensitive material for electrophoretic imaging processes in U.S. Pat. No. 3,615,558 by Tulagin et al. have long been known to exhibit useful photoconductive properties.

SUMMARY OF THE INVENTION

The present invention provides a novel group of methine colorant particulate materials which are useful in electrophoretic migration imaging layers, images and processes.

The novel colorants of this invention have the general formula or (I)        (II)

wherein $R^1$ is hydrogen, lower alkyl, lower alkoxy, nitro, halogen, cyano, phenyl, lower alkylsulfonamido or lower alkoxycarbonyl and $A^1$ is a monovalent and $A^2$ is a divalent residue of an aniline, 1,2,3,4-tetrahydroquinoline, benzomorpholine or indoline compound attached to the =CH— group by an aromatic ring carbon atom in the position para to the aromatic amine nitrogen atom. The aniline, 1,2,3,4-tetrahydroquinoline, benzomorpholine and indoline residues represented by $A^1$ and $A^2$ are well-known in the art of methine colorants as is evidenced by the following patents the disclosures of which are incorporated herein:

| U.S. Pat. No. | U.S. Pat. No. | U.S. Pat. No. | |
|---|---|---|---|
| 1,950,421 | 2,914,551 | 3,504,010 | |
| 2,053,819 | 3,027,220 | 3,555,016 | |
| 2,166,487 | 3,189,641 | 3,728,374 | |
| 2,179,895 | 3,240,783 | 3,829,436 | |
| 2,206,108 | 3,247,211 | 3,917,604 | |
| 2,583,551 | 3,326,960 British | 1,173,679 | |
| 2,649,471 | 3,349,098 | 1,138,583 | |
| 2,766,233 | 3,386,491 | 1,138,582 | |
| 2,776,310 | 3,390,168 | 1,053,997 | |
| 2,789,125 | 3,422,133 | 1,049,315 | |
| 2,811,544 | 3,435,062 | 1,036,097 | |
| 2,850,520 | 3,453,280 Belgian | 703,661 | |

Typical of such residues are the groups having the formulas

-continued in which $R^2$ is hydrogen, lower alkyl, lower alkoxy or halogen; n is 0, 1 or 2; $R^3$ and $R^4$ are unsubstituted or substituted alkyl containing up to about 12 carbon atoms; cyclohexyl; unsubstituted or substituted aryl; or when $R^4$ is phenyl $R^3$ can be hydrogen; $R^5$, $R^6$ and $R^7$ are hydrogen or lower alkyl; $R^8$ and $R^9$ are lower alkyl or aryl and $R^{17}$ is hydrogen or, when $R^5$, $R^6$ and $R^7$ each is hydrogen, $R^{17}$ can be halogen or a substituent derived from halogen or hydroxy groups such as those set forth hereinafter for $R^{17}$. As used herein to describe an alkyl group or a group containing an alkyl moiety, "lower" designates a carbon content of up to about 4 carbon atoms. The aryl groups referred to herein include phenyl and phenyl substituted with nonionic substituents such as lower alkyl, lower alkoxy, halogen, lower alkoxycarbonyl, cyano, carbamoyl, etc.

The $A^2$ moieties of the $—A^2—A^2—$ residues of methine compounds (II), i.e., bis-methine compounds, can be joined by a common nitrogen atom as disclosed in U.S. Pat. No. 3,189,641, or by various aliphatic groups which can contain within them aryl and cycloalkyl groups as disclosed in U.S. Pat. No. 3,386,591, U.S. Pat. No. 3,504,010, U.S. Pat. No. 3,597,434 and Belgian Pat. No. 703,661. Representative of the residues represented by $—A^2—A^2—$ are groups conforming to the formula wherein each $R^2$, $R^3$, $R^5$, $R^6$, $R^7$, $R^8$ and $R^9$ can be the same or different groups as defined above, m is 0 or 1 and E is a divalent group having the formula —$R^{11}$—G—$R^{12}$— in which $R^{11}$ and $R^{12}$ are lower alkylene groups and G is a divalent radical such as oxygen, sulfur, sulfonyl, a dicarboxylic acid ester residue, a diisocyanate residue, a dicarboxylic acid amide residue, etc. The group —$R^1$—$R^1$— also can be joined benzomorpholine groups or the $R^1$ groups can be different, e.g., an aniline residue joined to a tetrahydroquinoline residue.

DESCRIPTION OF THE PREFERRED EMBODIMENTS

The preferred compounds are those having formula (I) wherein $R^1$ is hydrogen and —$A^1$ has the general formula wherein
$R^{13}$ is hydrogen, methyl, methoxy, ethoxy or chlorine;
$R^{14}$ is hydrogen, methyl, methoxy or ethoxy;
$R^3$ is lower alkyl, phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula $$\underset{Y}{\overset{O}{\underset{\|}{-N}\overset{\|}{\overset{C}{\diagdown}}R^{16}}}$$

in which Y is —CO—, —$SO_2$—, or —$CH_2$— and $R^{16}$ is ethylene, propylene, trimethylene or o-arylene;
$R^4$ is lower alkyl; cyclohexyl; lower alkylcyclohexyl; benzyl; benzyl substituted with lower alkyl, lower alkoxy, chlorine or bromine; aryl; or a group having the formula —$R^{11}$—$R^{17}$ in which $R^{11}$ is ethylene, propylene, trimethylene or tetramethylene and $R^{17}$ is lower alkanoyloxy, lower alkoxycarbonyloxy, aroyloxy or lower alkoxy;

$R^8$, $R^9$ and $R^{10}$ each is hydrogen or methyl; and
$R^{17}$ is hydrogen or, when $R^8$, $R^9$ and $R^{10}$ each is hydrogen, $R^{17}$ is a substituent represented by $R^{15}$;
in which each aryl moiety is phenyl, tolyl, lower alkoxyphenyl, or chlorophenyl.

The novel methine colorants of this invention are prepared by condensing a thiazolo[3,2-a]benzimidazol-3(2H)-one having the structure with an aromatic aldehyde or bis-aldehyde having the formula OHC—$A^1$ or OHC—$A^2$—$A^2$—CHO. The compounds of formula (III) can be obtained by the following procedure Also, see J. Heterocyclic Chem., 14, 1093 (1977), J. Am. Chem. Soc., 78, 5831 (1956) and Ind. J. Chem., 10, 175 (1972). The aromatic aldehydes having the formulas OHC—$A^1$ and OHC—$A^2$—A—CHO are prepared by formylating aromatic amines having the formulas H—$A^1$ and H—$A^2$—$A^2$—H according to procedures well-known in the art.

The novel methine colorants are further illustrated by the following examples.

EXAMPLE 1

Chloroacetic acid (56.5 g, 0.59 m), 2-mercaptobenzimidazole (89 g, 0.59 m), and anhydrous sodium acetate (49.3 g, 0.59 m) were combined in 900 ml of 2B ethanol and heated on a steam bath for three hours. The solution volume was condensed under reduced pressure to approximately 300 ml and poured into 1200 ml of water. The solid was collected by filtration, washed with water, and air-dried, to yield 109.7 g (0.525 m, 89%) of benzimidazol-2-thioacetic acid as a white powder, melting point 211°–212° C. (dec.).

Benzimidazol-2-thioacetic acid (108 g, 0.52 m) was slurried in pyridine (360 ml) and heated on a steam bath. Acetic anhydride (54.6 ml) was added dropwise to the reaction mixture and a dark, homogeneous solution was gradually obtained. Heating was continued for one hour after addition was complete and the solution was cooled and poured into 1200 ml of water. The solid was collected by filtration, washed with water, and air-dried to yield 83.5 g (0.44 m, 85%) of thiazolo[3,2-a]benzimidazol-3(2H)-one.

EXAMPLE 2

Phenyl isocyanate (99 ml, 0.75 m + 10% excess) and N-(β-hydroxyethyl)-3,6-dimethyl-1,4-benzomorpholine (155.2 g, 0.75 m) were combined in 750 ml of dimethylformamide and heated on a steam bath. The progress of the reaction was followed by TLC (CHCl₃) visualized with diazo spray, and was complete in 1½–2 hours. The reaction mixture was cooled to 10° C. and treated dropwise with phosphorus oxychloride (75 ml, 0.75 m) at 10°–20° C. When addition was complete, the reaction mixture was heated on a steam bath and followed by TLC (CHCl₃) with visualization by UV light and diazo spray until a single product was present that did not visualize with the spray (about two hours). The reaction mixture was poured into approximately 4 liters of ice and water containing about 100 ml of concentrated NH₄OH and stirred for ½ hour. Additional base was added as needed during the drowning and stirring steps to keep the mixture pH 7–8. The solution was decanted and the solid and gummy residue was rinsed with fresh water and triturated with 500 ml of hot 2B ethanol. When the gummy residue had been digested the mixture was cooled. The solid product having the structure was isolated by filtration, washed with cold 2B ethanol, and air-dried to yield 171.8 g (0.49 m, 65%) of the desired product as a pale yellow powder, melting point 124.5°–126.5° C. The additional crops of product were recovered by condensing the filtrate to give a total yield of 219 g (0.62 m, 83%).

EXAMPLE 3

Thiazolo[3,2-a]benzimidazol-3(2H)-one (76 g, 0.4 m) and N-(β-phenylcarbamoylethyl)-3,6-dimethyl-7-formyl-1,4-benzomorpholine (142 g, 0.4 m) were combined in 1200 ml of glacial acetic acid followed by the addition of 6.4 ml of piperidine. The mixture was refluxed for 7 hours and allowed to cool. The solid was collected by filtration, washed with acetic acid and ethanol, and air-dried to yield 166 g (0.32 m, 79%) of the methine colorant having the structure as a bright yellow-orange powder.

When tested for migration imaging according to the procedure described hereinafter, this colorant exhibited excellent photoelectrophoretic activity and color selectivity. It has a max of 457 nm as determined in an acetone solution of the colorant.

The following examples of the novel colorants of this invention were prepared according to procedures similar to that set forth above. The colorants which conform to formulas I or II wherein $R^1$ is hydrogen exhibit good to excellent photoelectroploretic activity.

| Example | $A^1/A^2$—$A^2$—CH= | Lambda max, nm |
|---|---|---|
| 4 |  | 458 |
| 5 |  | 456 |
| 6 |  | 453 |

-continued

| Example | $A^1/A^2-A^2-CH=$ | Lambda max, nm |
|---|---|---|
| 7 |  | 459 |
| 8 |  | 460 |
| 9 |  | 457 |
| 10 |  | 458 |
| 11 |  | 454 |
| 12 |  | 453 |

-continued

| Example | $A^1/A^2-A^2-CH=$ | Lambda max, nm |
|---|---|---|
| 13 |  | 448 |
| 14 |  | 445 |
| 15 |  | 445 |
| 16 |  | 440 |
| 17 |  | 445 |
| 18 |  | 435 |
| 19 |  | 438 |
| 20 |  | 450 |

-continued

| Example | $A^1/A^2-A^2-CH=$ | Lambda max, nm |
|---|---|---|
| 21 | [structure with N(C₂H₅)₂ group, two CH₃ groups, and N-C₂H₅] | 450 |
| 22 | [structure with CH₃-NC₂H₅ group, two CH₃ groups, and N-CH₃] | 450 |
| 23 | [structure with OCNHC₆H₅ group, CH₃, and N-C₂H₅] | 452 |
| 24 | [structure with OCNHC₆H₅ group, CH₃, and N-CH₂CH₂OCNHC₆H₅] | 449 |

The present invention also provides an electrophoretic migration image recording method comprising the steps of:
(a) providing an electrically photosensitive imaging layer comprising an electrically photosensitive material having formula (I) or (II);
(b) applying an electric field across said layer;
(c) exposing said layer to an image pattern of electromagnetic radiation to which said electrically photosensitive layer is photosensitive; and
(d) if necessary, at least partially, liquifying said layer before, during or after exposure and application of the electric field to facilitate at least minimum migration of said electrically photosensitive material in said layer
thereby forming a record of the image pattern of electromagnetic radiation in said layer.

As will be more fully explained hereinafter, the image record formed by this method may be a latent image or developed visual image.

The electrically photosensitive particulate materials of formulas (I) and (II) are useful in all electrophoretic migration imaging layers and processes which requires the combined action of an electric field and exposure to an image pattern of electromagnetic radiation to obtain an image. The formulas (I) and (II) materials are also useful in the imaging processes such as described in U.S. Pat. Nos. 3,520,681; 3,770,430; 3,795,195; 4,013,462; 3,707,368; 3,692,576 and 3,756,812, all relating to manifold imaging or photoelectrosolography.

In an exemplary embodiment of one such process an element comprising a conductive substrate or a substrate having a conductive layer in electrical contact with a liquified or partially liquified electrically photosensitive imaging layer is imaged in the following manner. A latent image is formed on the layer, for example, by uniformyl electrostatically charging and exposing it to an image pattern of activating electromagnetic radiation. The electrically photosensitive particles in the layer which have been exposed to radiation migrate through the imaging layer leaving a latent image record of the image pattern on the conductive substrate. This latent image is developed by submerging the element in a solvent which removes or dissolves the exposed, or the unexposed portions of the layer.

In another migration imaging processes the electrically photosensitive layers contain a liquid or at least partially liquid electrically photosensitive imaging layer sandwiched between two support sheets to form an imaging element. The element is positioned between two electrodes. An electric field is applied across the imaging layer and the imaging layer is exposed to an image pattern of activating electromagnetic radiation causing the electrically photosensitive particulate material in the imaging layer to migrate imagewise thereby forming a latent image recording of the image pattern. Upon separation of the two sheets, in an electric field a visual record of the image pattern is formed on at least one of the two sheets.

The structure of the imaging elements can take many forms. For example, the element may include separate electrodes on opposite sides of the donor two sheets for the application of the field or they may be directly on the back surfaces of the sheet members and integral therewith. Alternatively, one or both of the sheets may be made of a conductive material. Conventionally, at least one of the sheets is transparent so as to permit exposure of the imaging layer.

In photoelectrophoretic migration imaging, a liquid or at least a partialy liquid electrically photo-sensitive imaging layer is positioned between two spaced electrodes. While so positioned between the spaced electrodes, the layer is subjected to an electric field and exposed to an image pattern of activating radiation. As a consequence, the charge-bearing, electrically photosensitive particles in the imaging undergo a radiation-induced variation in their charge polarity and migrate to one or the other of the electrode surfaces to form on at least one of the electrodes an image pattern representing a positive-sense or negative-sense image of the original image pattern.

In each of the foregoing processes, the electrically photosensitive imaging layers are at least partially liquid or can be rendered at least partially liquid. The phrase partially liquid is used herein to mean that the cohesive forces of materials forming the layer are sufficiently weak or weakened to permit some imagewise migration, under the combined influence of exposure and an electric field, in the layer of the electrically photosensitive particulate material to form a record of the imaging radiation in the layer.

In general, layers which are not at least partially liquid may be rendered at least partially liquid by treatment with, for example, heat, a solvent or solvent vapors before, during or after the exposure to an image pattern of electromagnetic radiation and application of an electric field. It will be clear to those skilled in the electrophoretic migration imaging art, that at least partial liquification of the layer before or during the application of the field and exposure will achieve results substantially identical to those obtained with a layer which is at least partially liquified to begin with. The liquification step may also take place sometime subsequent to the exposure and field application steps with good results. In the latter situation, the layer is liquified in the presence of a second electric field and the latent image developed according to one of the techniques previously mentioned herein.

The extent to which the electrically photosensitive particulate materials migrate in an electrically photosensitive imaging layer which must be liquified can be controlled by varying the time which the layer is exposed to a particular liquifying medium such as heat or solvent. If the layer is only slightly liquified, the electrically photosensitive material will migrate only slightly, thus forming a record which is a latent image, or image pattern. This layer containing the latent image can be stored and developed more fully at a later date. This delayed development can be carried out simply by placing the latent image containing layer in an electric field and then liquifying the layer sufficiently to allow the exposed electrically photosensitive material to migrate to an electrode or other substrate. Development of the visual record of the image pattern is then carried out according to one of the described techniques.

The electrically photosensitive layer of this invention in general comprises the formula (I) and (II) electrically photosensitive particulate materials dispersed in an electrically insulating carrier material such as an electrically insulating liquid, or an electrically insulating, liquefiable matrix material, such as a heat- and/or solvent-liquefiable polymeric material or a thixotropic polymeric material. Typically, when one employs such a dispersion of electrically photosensitive particulate material and electrically insulating carrier material between the spaced electrodes of an electrophoretic migration imaging system, it is conventional to employ from about 0.05 part to about 2.0 parts of electrically photosensitive particulate material for each 10 parts by weight of electrically insulating carrier material.

The carrier material may assume a variety of physical forms and may be selected from a variety of different materials. For example, the carrier material may be a matrix of an electrically insulating, normally solid polymeric material capable of being at least partially liquefied. Useful liquifiable electrically insulating carriers are disclosed in aforementioned U.S. Pat. Nos. 3,520,681; 3,975,195; 4,013,462; 3,707,368; 3,692,516 and 3,756,812. The carrier material can comprise an electrically insulating liquid such as decane, paraffin, Sohio Odorless Solvent 3440 (a kerosene fraction marketed by the Standard Oil Company, Ohio), various isoparaffinic hydrocarbon liquids such as those sold under the trademark Isopar G by Exxon Corporation and having a boiling point in the range of 145° C. to 186° C., various halogenated hydrocarbons such as carbon tetrachloride, trichloromonofluoromethane, and the like, various alkylated aromatic hydrocarbon liquids such as the alkylated benzenes, for example, xylenes, and other alkylated aromatic hydrocarbons such as are described in U.S. Pat. No. 2,899,335. An example of one such useful alkylated aromatic hydrocarbon liquid which is commercially available in Solvesso 100 made by Exxon Corporation. Solvesso 100 has a boiling point in the range of about 157° C. to about 177° C. and is composed of 9 percent dialkyl benzenes, 37 percent trialkyl benzenes, and 4 percent aliphatics. Typically, whether solid or liquid at normal room temperatures, i.e., about 22° C., the electrically insulating carrier material used in the present invention is a material having a resistivity greater than about $10^9$ ohm-cm, preferably greater than about $10^{12}$ ohm-cm.

In general, electrically photosensitive particulate material useful in electrophoretic migration imaging layers and processes have an average particle size within the range of from about 0.01 micron to about 20 microns, preferably from about 0.01 to about 5 microns. Typically, these particles are composed of one or more colorant materials such as the electrically photosensitive colorant materials of Formula I. However, these electrically photosensitive particles may also contain various non-photosensitive materials such as electrically insulating polymers, charge control agents, various organic and inorganic fillers, as well as various additional dyes or pigment materials to change or enhance various colorant and physical properties of the electrically photosensitive particle. In addition, such electrically photosensitive particles may contain other photosensitive materials such as various sensitizing dyes and/or chemical sensitizers to alter or enhance their response characteristics to activating radiation.

When the electrically photosensitive particles formed from the materials of the present invention are incorporated in a carrier material, such as one of the above-described electrically insulating liquids, various other addenda may also be incorporated in the resultant imaging dispersions.

For example, various charge control agents may be incorporated in such a suspension to improve the uniformity of charge polarity of the electrically photosensitive particles dispersed in the liquid suspension. Charge control agents are typically polymeric materials incorporated by admixture thereof into the liquid carrier vehicle of the suspension. In addition to, and possibly related to, the aforementioned enhancement of uniform charge polarity, it has been found that the charge control agents often provide more stable suspensions, i.e., suspensions which exhibit substantially less settling out of the dispersed photosensitive particles. Illustrative charge control agents include those disclosed in copending U.S. Patent Application 837,779 filed Sept. 29, 1977, by Stahly. The polymeric charge control agents disclosed therein comprise a copolymer having at least two different repeating units, (a) one of said units being present in an amount of at least about $0.5 \times 10^{-4}$ moles/gram of said copolymer and being derived from monomers selected from the group consisting of metal salts of sulfalkyl acrylates and methacrylates and metal salts of acrylic and methacrylic acids, and (b) one of said repeating units being derived from monomers soluble in said carrier vehicle and present in an amount sufficient to render said copolymer soluble in said carrier vehicle.

Examples of such copolymers are poly(vinyltoluene-co-lauryl methacrylate-co-lithium methacrylate-co-methacrylic acid), poly(styrene-co-lauryl methacrylate-co-lithium sulfoethyl methacrylate), poly(vinyltoluene-co-lauryl methacrylate-co-lithium methacrylate), poly(t-butylstyrene-co-lauryl methacrylate-co-lithium methacrylate-co-methacrylic acid) or poly(t-butylstyrene-co-lithium methacrylate).

In addition to the foregoing charge control agent materials, various polymeric binder materials such as various natural, semi-synthetic or synthetic resins, may be dispersed or dissolved in the electrically insulating carrier to serve as a fixing material for the final photosensitive particle image formed on one of the spaced electrodes used in electrophoretic migration imagining systems. Here again, the use of such fixing addenda is conventional and well known in the closely related art of liquid electrographic developer compositions so that extended discussion thereof is unnecessary herein.

The utility of the materials of formula (I) and (II) in an electrophoretic migration imaging process will be described in more detail with reference to the accompanying drawing, FIG. 1, which illustrates a typical apparatus for carrying out electrophoretic migration imaging processes.

Figure 1:
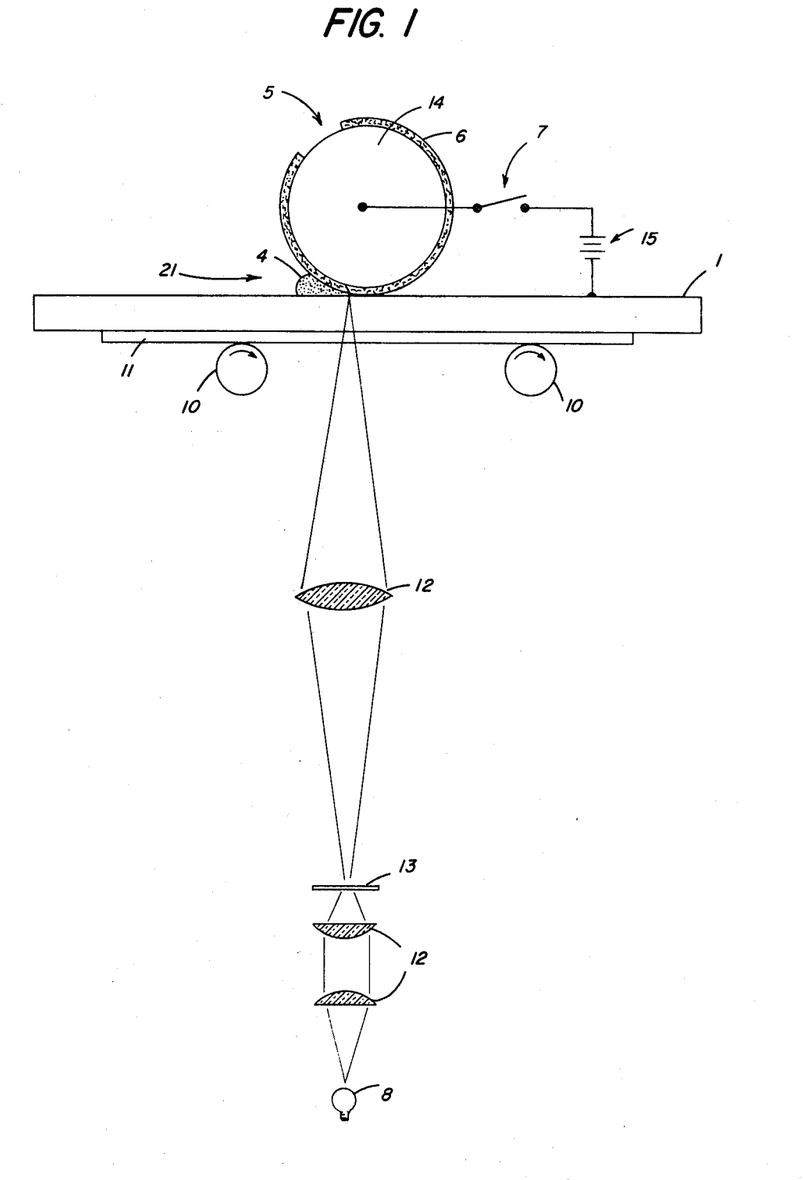
The FIGURE represents diagrammatically a typical imaging apparatus for carrying out the electrophoretic migration imaging process of the invention.

FIG. 1 shows a transparent electrode 1 supported by two rubber drive rollers 10 capable of imparting a translating motion via original image 11 to electrode 1 in the direction of the arrow. Electrode 1 may be composed of a layer of optically transparent material, such as glass or an electrically insulating, transparent polymeric support such as polyethylene terephthalate, covered with a thin, optically transparent, conductive layer such as tin oxide, indium oxide, nickel, and the like. Optionally, depending upon the particular type of electrophoretic migration imaging process desired, the surface of electrode 1 may bear a "dark charge exchange" material, such as a solid solution of an electrically insulating polymer and 2,4,7,trinitro-9-fluorenone as described by Groner in U.S. Pat. No. 3,976,485 issued Aug. 24, 1976 and incorporated herein by reference.

Spaced opposite electrode 1 and in pressure contact therewith is a second electrode 5, an idler roller which serves as a counter electrode to electrode 1 for producing the electric field used in the exemplified electrophoretic migration imaging process. Typically, electrode 5 has on the surface thereof a thin, electrically insulating layer 6. Electrode 5 is connected to one side of the power source 15 by switch 7. The opposite side of the power source 15 is connected to electrode 1 so that as an exposure takes place, switch 7 is closed and an electric field is applied to the electrically photosensitive particulate material 4 which is positioned between electrodes 1 and 5. Typically, electrically photosensitive particulate material 4 is dispersed in an electrically insulating carrier material such as described hereinabove.

The electrophoretic migration imaging layer 4 may be formed between electrodes 1 and 5 by applying a dispersion containing a Formula I electrically photosensitive particulate material to either or both of the surfaces of electrodes 1 and 5 prior to the imaging process or by placing the dispersion between electrodes 1 and 5 during the electrophoretic migration imaging process.

As shown in FIG. 1, exposure of layer 4 takes place by use of an exposure system consisting of light source 8, an original image 11 to be reproduced, such as a photographic transparency, a lens system 12, and any necessary or desirable radiation filters 13, such as color filters, whereby layer 4 is irradiated with a pattern of activating radiation corresponding to original image 11. Although the electrophoretic migration imaging system represented in FIG. 1 shows electrode 1 to be transparent to activating radiation from light source 8, it is possible to irradiate layer 4 in the nip 21 between electrodes 1 and 5 without either of electrodes 1 or 5 being transparent. In such a system, although not shown in FIG. 1, the exposure source 8 and lens system 12 is arranged so that image material 4 is exposed in the nip or gap 21 between electrodes 1 and 5.

As shown in FIG. 1, electrode 5 is a roller electrode having a conductive core 14 connected to power source 15. The core is in turn covered with a layer of insulating material 6, for example, baryta paper. Insulating material 6 serves to prevent or at least substantially reduce the capability of electrically photosensitive material in layer 4 to undergo a radiation induced charge alteration upon interaction with electrode 5. Hence, the term "blocking electrode" may be used, as is conventional in the art of electrophoretic migration imaging, to refer to electrode 5.

Although electrode 5 is shown as a roller electrode and electrode 1 is show as essentially a translatable, flat transparent plate electrode in FIG. 1, either or both of these electrodes may assume a variety of different shapes such as a web electrode, rotating drum electrode, opaque plate electrode, and the like as is well known in the field of electrophoretic migration imaging. In general, during a typical electrophoretic migration imaging process wherein layer 4 comprises electrically photosensitive particulate material dispersed in an electrically insulating, liquid carrier, electrodes 1 and 5 are spaced such that they are in pressure contact or very close to one another during the electrophoretic migration imaging process, e.g., less than 50 microns apart. However, where the electrically photosensitive particulate material is simply dispersed without a liquid carrier in an air gap between electrodes 1 and 5 or in a carrier such as a layer of heat- or solvent-liquefiable material coated as a separate layer on electrode 1 and/or 5, these electrodes may be spaced more than 50 microns apart during the imaging process.

The strength of the electric field imposed between electrodes 1 and 5 during the electrophoretic migration imaging process may vary considerably; however, it has generally been found that optimum image density and resolution are obtained by increasing the field strength to as high a level as possible without causing electrical breakdown of the carrier medium in the electrode gap. For example, when electrically insulating liquids such as isoparaffinic hydrocarbons are used as the carrier in the imaging apparatus of FIG. 1, the applied voltage across electrodes 1 and 5 typically is within the range of from about 100 volts to about 4 kilovolts or higher.

As explained hereinabove, image formation occurs in electrophoretic migration imaging processes as the result of the combined action of activating radiation and electric field on the electrically photosensitive particulate material disposed between electrodes 1 and 5 in the attached drawing. Typically, for best results, field application and exposure to activating radiation occur concurrently. However, as would be expected, by appropriate selection of various process parameters such as field strength, activating radiation intensity, incorporation of suitable light sensitive addenda in or togther with the electrically photosensitive particles formed from the materials of Formula I, e.g., by incorporation of a persistent photoconductive material, and the like, it is possible to alter the timing of the exposure and field application events so that one may use sequential exposure and field application events rather than concurrent field application and exposure events.

When disposed between imaging electrodes 1 and 5 of FIG. 1, electrically photosensitive particulate material 4 in layer 4 exhibits an electrostatic charge polarity, either as a result of triboelectric interaction of the particles or as a result of the particles interacting with the carrier material in which they are dispersed, for example, an electrically insulating liquid, such as occurs in conventional liquid electrographic developing compositions composed of toner particles which acquire a charge upon being dispersed in an electrically insulating carrier liquid.

Image discrimination occurs in photoelectrophoretic imaging processes as a result of the combined application of electric field and activating radiation on the electrically photosensitive particulate material layer 4 positioned between electrodes 1 and 5 of the apparatus shown in FIG. 1. That is, in a typical imaging operation, upon application of an electric field between electrodes 1 and 5, the particles of charge-bearing, electrically photosensitive material are attracted in the dark to either electrodes 1 or 5, depending upon which of these electrodes has a polarity opposite to that of the original charge polarity acquired by the electrically photosensitive particles. And, upon exposing layer 4 to activating electromagnetic radiation, it is theorized that there occurs neutralization or reversal of the charge polarity associated with either the exposed or unexposed particles. In typical electrophoretic migration imaging systems wherein electrode 1 bears a conductive surface, the exposed, electrically photosensitive particles 4, upon coming into electrical contact with such conductive surface, undergo an alternation (usually a reversal) of their original charge polarity as a result of the combined application of electric field and activating radiation. Alternatively, in the case of photoimmobilized electrophoretic recording (PIER), wherein the surface of electrode 1 bears a dark charge exchange material as described by Groner in aforementioned U.S. Pat. No. 3,976,485, one obtains reversal of the charge polarity of the unexposed particles, while maintaining the original charge polarity of the exposed electrically photosensitive particles, as these particles come into electrical contact with the dark charge exchange surface of electrode 1. In any case, upon the application of electric field and activating radiation to layer 4 disposed between electrodes 1 and 5 of the apparatus shown in FIG. 1, one cab effectively obtain image discrimination so that an image pattern is formed by the electrically photosensitive particle layer which corresponds to the original pattern of activating radiation. Typically, using the apparatus shown in FIG. 1, one obtains a visible image on the surface of electrode 1 and a complementary image pattern on the surface of electrode 5.

Subsequent to the application of the electric field and exposure to activating radiation, the images which are formed on the surface of electrodes 1 and/or 5 of the apparatus shown in FIG. 1 may be temporarily or permanently fixed to these electrodes or may be transferred to a final image receiving element. Fixing of the final particle image can be effected by various techniques, for example, by applying a resinous coating over the surface of the image bearing substrate. For example, if electrically photosensitive particles 4 are dispersed in a liquid carrier between electrodes 1 and 5, one may fix the image or images formed on the surface of electrodes 1 and/or 5 by incorporating a polymeric binder material in the carrier liquid. Many such binders (which are well known for use in liquid electrophotographic liquid developers) are known to acquire a charge polarity upon being admixed in a carrier liquid and therefore will, themselves, electrophoretically migrate to the surface of one or the other of the electrodes. Alternatively, a coating of resinous binder (which has been admixed in the carrier liquid), may be formed on the surface of electrodes 1 and/or 5 upon evaporation of the liquid carrier.

The electrically photosensitive colorant material of Formula I may be used to form monochrome images, or the material may be admixed with other electrically photosensitive material of proper color and photosensitivity and used to form polychrome images. Many of the electrically photosensitive colorant materials having Formula I have especially useful hues which make them particularly suited for use in polychrome imaging processes which employ a mixture of two or more differently colored electrically photosensitive particles. When such a mixture of multicolored electrically photosensitive particles is formed, for example, in an electrically insulating carrier liquid, this liquid mixture of particulate material exhibits a black coloraton. Preferably, the specific cyan, magenta, and yellow particles selected for use in such a polychrome imaging process are chosen so that their spectral response curves do not appreciably overlap whereby color separation and subtractive multicolor image reproduction can be achieved.

The following examples illustrate the utility of the Formula I materials in electrophoretic migration imaging processes.

EXAMPLES 25–46

Imaging Apparatus

An imaging apparatus was used in each of the following examples to carry out the electrophoretic migration imagining process described herein. This apparatus was a device of the type illustrated in FIG. 1. In this apparatus, a translating film base having a conductive coating of 0.1 optical density cermet (CR.SiO) served as electrode 1 and was in pressure contact with a 10 centimeter diameter aluminum roller 14 covered with dielectric paper coated with poly(vinyl butyral) resin which served as electrode 5. Plate 1 was supported by two 2.8 cm. diameter rubber drive rollers 10 positioned beneath film plate 1 such that a 2.5 cm. opening, symmetric with the axis of the aluminum roller 14, existed to allow exposure of electrically photosensitive particle 4 to activating radiation. The original transparency 11 to be reproduced with taped to the back side of film plate 1.

The original transparency to be reproduced consisted of adjacent strips of clear (W0), red (W29), green (W99) and blue (W47B) filters. The light source consisted of a Kodak Ektagraphic AV434A Carousel Projector with a 1000 watt Xenon Lamp. The light source consisted of a Kodak Ektagraphic AV434A Carousel Projector with a 1000 watt Xenon Lamp. The light was modulated with a Kodak No. 5 flexible M-carbon eleven step 0.3 neutral density step tablet. The residence time in the action or exposure zone was 10 milliseconds. The log of the light intensity (Log I) was as follows:

| Filters | | Log I erg/cm$^2$/sec. |
|---|---|---|
| W0 | Clear | 5.34 |
| W29 | Red | 4.18 |
| W99 | Green | 4.17 |
| W47B | Blue | 4.15 |

The voltage between the electrode 5 and film plate 1 was about 2 kv. Film plate 1 was negative polarity in the case where electrically photosensitive particulate material of layer 4 carried a positive electrostatic charge, and film plate 1 was positive in the case where electrically photosensitive electrostatically charged particles were negatively charged. The translational speed of film plate 1 was about 25 cm. per second. In the following examples, image formation occurs on the surfaces of film plate 1 and electrode 5 after simultaneous application of light exposure and electric field to electrically photosensitive layer 4 formed from the dispersion of electrically photosensitive particulate material of formulas (I) and (II) in a liquid carrier. The liquid imaging dispersion was placed in nip 21 between the electrodes 1 and 5. If the material being evaluated for use in layer 4 possessed a useful level of electrical photosensitivity, one obtained a negative-appearing image reproduction of original 11 on electrode 5 and a complementary image on electrode 1.

Imaging Dispersion Preparation

Imaging dispersions were prepared to evaluate each of the materials in Table I. The dispersions were prepared by first making a stock solution of the following components. The feed solution was prepared simply by combining the components.

| Isopar G | 2.2 g |
|---|---|
| Solvesso | 1.3 g |
| Piccotex 100 | 1.4 g |
| PVT* | 0.1 g |

*Poly(vinyltoluene-co-lauryl methacrylate-co-lithium methacrylate-co-methacrylic acid) 56/40/3.6/0.4

A 5 g. aliquot of the stock solution was combined in a closed container with 0.0456 g. of the Table I material to be tested and 12 g. of Pioneer 440 stainless steel balls. The preparation was then milled for three hours on a paint shaker.

Each of the materials described in Examples 3–24 were tested according to the just outlined procedures. Each of such material was found to be electrophotosensitive as evidenced by obtaining a negative appearing image of the original on one electrode and a complementary image on the other electrode. Image quality was determined visually having regard to minimum and maximum densities, speed and color saturation.

The invention has been described in detail with particular reference to certain preferred embodiments thereof, but it will be understood that variations and modifications can be effected within the spirit and scope of the invention.

We claim:

1. An electrophoretic migration imaging recording method comprising the steps of:
   (a) providing an electrically photosensitive imaging layer comprising an electrically photosensitive particulate material having the following general structure:

wherein $R^1$ is hydrogen, lower alkyl, lower alkoxy, nitro, halogen, cyano, phenyl, lower alkylsulfonamido or lower alkoxycarbonyl and $A^1$ is a monovalent and $A^2$ is a divalent residue of an aniline, 1,2,3,4-tetrahydroquinoline, benzomorpholine or indoline compound attached to the =CH— group by an aromatic ring carbon atom in the position para to the aromatic amine nitrogen atom,
   (b) applying an electrical field across said layer; and
   (c) exposing said layer to an image pattern of electromagnetic radiation to which said electrically photosensitive material is photosensitive; and
   (d) if necessary, at least partially liquifying said layer before, during or after exposure and application of the electric field to permit some migration of said electrically photosensitive material in said layer, thereby forming a record of the image pattern of electromagnetic radiation in said layer.

2. A method as in claim 1, further comprising the steps of:
   (a) positioning said layer between two electrodes during the exposure and application of the electric field; and then
   (b) separating the electrodes thereby forming a visual record of the image pattern of electromagnetic radiation on at least one of the electrodes.

3. A method as in claim 1, further comprising the steps of:
   (a) placing said layer between two support sheets to form an imaging element;
   (b) positioning the element between two electrodes during the exposure and application of the electric field; and
   (c) separating the two support sheets thereby forming a visual record of the image pattern of electromagnetic record on the support sheets.

4. A method as in claims 2 or 3, wherein said layer is liquified in the presence of an electric field some time subsequent to exposure.

5. A method as in claim 1, further comprising the step of developing a visual record of the image pattern of electromagnetic radiation by removing the exposed or unexposed portion of said layer.

6. A method as in claims 1, 2 or 3 wherein said electrically photosensitive particulate material has the structure wherein $R^1$ is hydrogen, lower alkyl, lower alkoxy, nitro, halogen, cyano, phenyl, lower alkylsulfonamido or lower alkoxycarbonyl and $A^1$ has the formula -continued in which $R^2$ is hydrogen, lower alkyl, lower alkoxy or halogen; n is 0, 1 or 2; $R^3$ and $R^4$ are unsubstituted or substituted alkyl containing up to about 12 carbon atoms; cyclohexyl; unsubstituted or substituted aryl; or when $R^4$ is phenyl $R^3$ can be hydrogen; $R^5$, $R^6$ and $R^7$ are hydrogen or lower alkyl; $R^8$ and $R^9$ are lower alkyl or aryl; $R^{17}$ is hydrogen or, when $R^5$, $R^6$ and $R^7$ each is hydrogen, $R^{17}$ is halogen derived from halogen or hydroxy.

7. A method as in claim 6 wherein said material has the structure wherein
$R^{13}$ is hydrogen, methyl, methoxy, ethoxy or chlorine;
$R^{14}$ is hydrogen, methyl, methoxy or ethoxy;
$R^3$ is lower alkyl, phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO₂—, or —CH₂— and $R^{16}$ is ethylene, propylene, trimethylene or o-arylene; and
$R^4$ is lower alkyl; cyclohexyl; lower alkylcyclohexyl; benzyl; benzyl substituted with lower alkyl, lower alkoxy, chlorine or bromine; aryl; or a group having the formula —$R^{11}$—$R^{17}$ in which $R^{11}$ is ethylene, propylene, trimethylene or tetramethylene and $R^{17}$ is lower alkanoyloxy, lower alkoxycarbonyloxy, aroyloxy or lower alkoxy, in which each aryl moiety is phenyl, tolyl, lower alkoxyphenyl, or chlorophenyl.

8. A method as in claim 6 wherein said material has the structure wherein $R^{13}$ is hydrogen, methyl, methoxy, ethoxy or chlorine;

$R^3$ is lower alkyl, phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO$_2$—, or —CH$_2$— and $R^{16}$ is ethylene, propylene, trimethylene or o-arylene;

$R^8$, $R^9$ and $R^{10}$ each is hydrogen or methyl; and $R^{17}$ is hydrogen or, when $R^8$, $R^9$ and $R^{10}$ each is hydrogen, $R^{17}$ is one of the substituents which $R^{15}$ can represent;

in which each aryl moiety is phenyl, tolyl, lower alkoxyphenyl, or chlorophenyl.

9. A method as in claim 6 wherein said material has the structure wherein $R^{13}$ is hydrogen, methyl, methoxy, ethoxy or chlorine;

$R^3$ is lower alkyl, phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO$_2$—, or —CH$_2$— and $R^{16}$ is ethylene, propylene, trimethylene or o-arylene;

$R^9$ is hydrogen or methyl;

in which each aryl moiety is phenyl, tolyl, lower alkoxyphenyl, or chlorophenyl.

10. A method as in claim 6 wherein said material has the structure wherein $R^{13}$ is hydrogen, methyl, methoxy, ethoxy or chlorine;

$R^3$ is lower alkyl, phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO$_2$—, or —CH$_2$— and $R^{16}$ is ethylene, propylene, trimethylene or o-arylene;

$R^4$ is lower alkyl; cyclohexyl; lower alkylcyclohexyl; benzyl; benzyl substituted with lower alkyl, lower alkoxy, chlorine or bromine; aryl; or a group hav- ing the formula —R[11]—R[17] in which R[11] is ethylene, propylene, trimethylene or tetramethylene and R[17] is lower alkanoyloxy, lower alkoxycarbonyloxy, aroyloxy or lower alkoxy;

in which each aryl moiety is phenyl, tolyl, lower alkoxyphenyl, or chlorophenyl.

11. A method as in claim 6 wherein said material is selected from the group consisting of -continued 12. An electrophoretic migration imaging layer comprising an electrically photosensitive particulate material having the structure wherein $R^1$ is hydrogen, lower alkyl, lower alkoxy, nitro, halogen, cyano, phenyl, lower alkylsulfonamido or lower alkoxycarbonyl and $A^1$ is a monovalent and $A^2$ is a divalent residue of an aniline, 1,2,3,4-tetrahydroquinoline, benzomorpholine or indoline compound attached to the =CH— group by an aromatic ring carbon atom in the position para to the aromatic amine nitrogen atom.

13. A layer as in claim 12 wherein said material has the structure wherein $R^1$ is hydrogen, lower alkyl, lower alkoxy, nitro, halogen, cyano, phenyl, lower alkylsulfonamido or lower alkoxycarbonyl and $A^1$ has the formula

-continued in which $R^2$ is hydrogen, lower alkyl, lower alkoxy or halogen; n is 0, 1 or 2; $R^3$ and $R^4$ are unsubstituted or substituted alkyl containing up to about 12 carbon atoms; cyclohexyl; unsubstituted or substituted aryl; or when $R^4$ is phenyl $R^3$ can be hydrogen; $R^5$, $R^6$ and $R^7$ are hydrogen or lower alkyl; $R^8$ and $R^9$ are lower alkyl or aryl; $R^{17}$ is hydrogen or, when $R^5$, $R^6$ and $R^7$ each is hydrogen, $R^{17}$ is halogen derived from halogen or hydroxy.

14. A layer as in claim 13 wherein said material has the structure wherein
$R^{13}$ is hydrogen, methyl, methoxy, ethoxy, or chlorine;
$R^{14}$ is hydrogen, methyl, methoxy or ethoxy;
$R^3$ is lower alkyl, phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO$_2$—, or —CH$_2$— and $R^{16}$ is ethylene, propylene, trimethylene or o-arylene; and
$R^4$ is lower alkyl; cyclohexyl; lower alkylcyclohexyl; benzyl; benzyl substituted with lower alkyl, lower alkoxy, chlorine or bromine; aryl; or a group having the formula —$R^{11}$—$R^{17}$ in which $R^{11}$ is ethylene, propylene, trimethylene or tetramethylene and $R^{17}$ is lower alkanoyloxy, lower alkoxycarbonyloxy, aroyloxy or lower alkoxy,
in which each aryl moiety is phenyl, tolyl, lower alkoxyphenyl, or chlorophenyl.

15. A layer as in claim 13 wherein said material has the structure wherein
$R^{13}$ is hydrogen, methyl, methoxy, ethoxy or chlorine;
$R^3$ is lower alkyl, phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO$_2$—, or —CH$_2$— and $R^{16}$ is ethylene, propylene, trimethylene or o-arylene;
$R^8$, $R^9$ and $R^{10}$ each is hydrogen or methyl; and
$R^{17}$ hydrogen or, when $R^8$, $R^9$ and $R^{10}$ each is hydrogen, $R^{17}$ is one of the substituents which $R^{15}$ can represent;
in which each aryl moiety is phenyl, tolyl, lower alkoxyphenyl, or chlorophenyl.

16. A layer as in claim 13 wherein said material has the structure wherein
R[13] is hydrogen, methyl, methoxy, ethoxy or chlorine;
R[3] is lower alkyl, phenethyl; cyclohexylmethyl; benzyl; benzyl substituted with lower alkyl, lower alkoxy, chlorine, bromine or lower alkoxycarbonyl; aryl; or a group having the formula —R[11]—R[15] in which R[11] is ethylene, propylene, trimethylene or tetramethylene and R[15] is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO$_2$—, or —CH$_2$— and R[16] is ethylene, propylene, trimethylene or o-arylene;
R[9] is hydrogen or methyl;
in which each aryl moiety is phenyl, tolyl, lower alkoxyphenyl, or chlorophenyl.

17. A layer as in claim 13 wherein said material has the structure wherein
R[13] is hydrogen, methyl, methoxy, ethoxy or chlorine;
R[3] is lower alkyl, phenethyl; cyclohexylmethyl; benzyl; benzyl substituted with lower alkyl, lower alkoxy, chlorine, bromine or lower alkoxycarbonyl; aryl; or a group having the formula —R[11]—R[15] in which R[11] is ethylene, propylene, trimethylene or tetramethylene and R[15] is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula in which Y is —CO—, —SO$_2$—, or —CH$_2$— and R[16] is ethylene, propylene, trimethylene or o-arylene;
R[4] is lower alkyl; cyclohexyl; lower alkylcyclohexyl; benzyl; benzyl substituted with lower alkyl, lower alkoxy, chlorine or bromine; aryl; or a group having the formula —R[11]—R[17] in which R[11] is ethylene, propylene, trimethylene or tetramethylene and R[17] is lower alkanoyloxy, lower alkoxycarbonyloxy, aroyloxy or lower alkoxy;
in which each aryl moiety is phenyl, tolyl, lower alkoxyphenyl, or chlorophenyl.

18. A layer as in claim 13 wherein said material is selected from the group consisting of 19. An electrophoretic migration image comprising an electrically photosensitive particulate material having the structure wherein $R^1$ is hydrogen, lower alkyl, lower alkoxy, nitro, halogen, cyano, phenyl, lower alkylsulfonamido or lower alkoxycarbonyl and $A^1$ is a monovalent and $A^2$ is a divalent residue of an aniline, 1,2,3,4-tetrahydroquinoline, benzomorpholine or indoline compound attached to the =CH— group by an aromatic ring carbon atom in the position para to the aromatic amine nitrogen atom.

* * * * *